United States Patent
Wong et al.

(10) Patent No.: US 6,261,497 B1
(45) Date of Patent: Jul. 17, 2001

(54) METHOD FOR PREPARATION OF CONTROLLED PORE GLASS-SYNTHETIC RESIN MEMBRANE

(75) Inventors: Yuan N. Wong, Boonton; Richard Chen, Livingston, both of NJ (US)

(73) Assignee: CPG, Inc., NJ (US)

( * ) Notice: Subject to any disclaimer, the term of this patent is extended or adjusted under 35 U.S.C. 154(b) by 0 days.

(21) Appl. No.: 09/305,219

(22) Filed: May 4, 1999

Related U.S. Application Data

(62) Division of application No. 08/604,440, filed on Feb. 21, 1996, now Pat. No. 5,904,848.

(51) Int. Cl.⁷ .................................................. B29C 67/04
(52) U.S. Cl. ........................... 264/120; 264/127; 264/345
(58) Field of Search .............................. 210/600, 500.26, 210/510.1, 500.36, 503, 502.1; 264/125, 340, 345, 127, 120, 122; 73/38

(56) References Cited

U.S. PATENT DOCUMENTS

| | | |
|---|---|---|
| 3,556,161 * | 1/1971 | Roberts . |
| 3,890,417 | 6/1975 | Vallance . |
| 4,153,661 | 5/1979 | Ree . |
| 4,373,519 | 2/1983 | Errede . |
| 4,460,642 | 7/1984 | Errede . |
| 4,565,663 | 1/1986 | Errede . |
| 4,609,383 | 9/1986 | Bonaventura . |
| 4,810,381 * | 3/1989 | Hagen et al. . |
| 4,923,901 | 5/1990 | Koester . |
| 4,971,736 | 11/1990 | Hagen . |
| 5,158,680 | 10/1992 | Kawai . |
| 5,478,893 | 12/1995 | Ghosh . |
| 5,647,985 * | 7/1997 | Ung-Chhun et al. . |
| 5,776,353 * | 7/1998 | Palm et al. . |

* cited by examiner

*Primary Examiner*—Ana Fortuna
*Assistant Examiner*—Richard W. Ward
(74) *Attorney, Agent, or Firm*—Cowan, Liebowitz & Latman, P.C.; Michael I. Wolfson

(57) ABSTRACT

Particulate inorganic pore material, e.g., controlled pore glass (CPG) embedded porous synthetic resin membrane is prepared by mixing inorganic pore material and an aqueous resin, preferably polytetrafluoroethylene (PTFE), aqueous dispersion to form a paste-like mass, heating the mass at a temperature between 50 to 70° C., and forming the mass into a sheet by calendering. The sheet is then sintered to produce a rigid porous sheet. The membrane may be functionalized, as by silanization. The membrane is useful for the same purposes as controlled pore glass or functionalized controlled pore glass.

6 Claims, No Drawings

METHOD FOR PREPARATION OF CONTROLLED PORE GLASS-SYNTHETIC RESIN MEMBRANE

This is is a divisional of application Ser. No. 08/604,440 filed on Feb. 21, 1996, now U.S. Pat. No. 5,904,848.

TECHNICAL FIELD

This invention relates to porous, synthetic resin membranes having particulate inorganic porous material embedded therein, to methods for the production of such membranes, and to the use of such membranes in various biotechnical procedures.

BACKGROUND OF THE INVENTION

One form of particulate inorganic porous material useful in the invention is controlled pore glass (CPG) described in U.S. Pat. Nos. 3,549,524 and 3,758,284 commercially available from CPG, Inc., 3 Borinski Road, Lincoln Park, N.J. 07035. It is widely used in methods for the synthesis of nucleic acids and for the isolation or purification of nucleic acids and proteins.

U.S. Pat. No. 3,890,417 describes a method for making a porous diaphragm suitable for use in electrolytic cells. The diaphragm is formed as a sheet from aqueous polytetrafluoroethylene (PTFE) and a solid, non-porous particle additive. Porosity is imparted to the product by removal of the particulate additive. U.S. Pat. No. 4,153,661 describes a similar method for making high tensile strength PTFE composite sheet material from aqueous PTFE, and organic or inorganic particles which comprises mixing and calendering at an elevated temperature (50–100° C.) to produce a self-supporting film for use as an electronic insulator.

U.S. Pat. Nos. 4,373,519, 4,460,642, 4,565,663 and 4,971,736 disclose methods for making water-swellable composite sheets having hydrophilic, absorptive particles enmeshed in the PTFE matrix for use as wound dressing and chromatographic supports.

DEFINITIONS

Particulate Inorganic Porous Material—Any particulate porous, inorganic material, preferably controlled pore glass (CPG). Particulate porous inorganic materials, including CPG have a particle size range of 0.1 to 200 microns and a pore diameter up to 4000 Å. Porous inorganic materials other than glass (CPG) include metal oxides such as aluminum oxide and titanium oxide.

Pore—A channel which may be closed or open-ended.

Pore Diameter—Cross section of a pore generally from about 40 Å to about 4000 Å.

Pore Volume—Volume of pores per unit mass of porous inorganic material generally at least 0.05 cc/g.

Synthetic Resin—Any non-naturally occurring, normally solid thermoplastic polymer, preferably polytetrafluoroethylene (PTFE) which is soluble or dispersible, for example as particles, in an aqueous medium.

Flow Rate—ml/min/cm$^2$ at 10 psi of acetonitrile through a 13 mm diameter membrane disc in a plastic Swinney disc filter holder.

Flow rate is particle size, pore diameter and pore volume dependent. In general, flow rate increases as a function of pore diameter and particle size. These factors are preferably selected to provide a flow rate of 20 to 200 ml/min/cm$^2$ of membrane.

Aqueous Resin—A solution of a synthetic resin or a suspension or dispersion of particulate synthetic resin in an aqueous medium which may contain a surfactant and in which the same or a different synthetic resin may be in solution. The preferred medium is water.

SUMMARY OF THE INVENTION

This invention provides a porous, synthetic resin, preferably PTFE, membrane having particulate inorganic porous material, preferably CPG embedded therein. The surfaces of the membrane may be modified, for example, by silanization to provide functional groups for the binding of biological moieties such as cells and biomolocules. Such functional groups include, but are not limited to amino, hydroxyl, carboxyl, epoxide, aldehyde, phenyl, and long chain, e.g., 5 to 50 carbon atom alkyl groups. The membranes of the invention, preferably functionalized, are useful inter alia in lieu of CPG as a support for the synthesis, isolation and purification of nucleic acids and for the isolation and purification of proteins.

DETAILED DESCRIPTION OF THE INVENTION

The particle size and pore diameter of the inorganic porous material utilized are selected to provide a membrane having a desired flow rate. In general, inorganic porous material having a particle size of 0.1 to 200 microns and a pore diameter from 40 Å to 4000 Å may be used.

Any synthetic resin may be utilized having due regard to the conditions, including reagents and temperature, to which the membrane will be subjected. Solid polyolefins such as polyethylene, polypropylene and polybutylene; vinyl resins such as polytetrafluoroethylene (PTFE), polyvinylchloride, polyvinylacetate and polymethylmethacrylate; polycarbonates and polysulfones are examples of suitable solid, thermoplastic resins. This disclosure is intended to include any and all solid, thermoplastic resins. PTFE is preferred.

To produce the membranes of the invention, inorganic porous material and the selected synthetic resin are appropriately combined in a dry or solid weight ratio of from 5% to 90%, preferably from 30% to 90% pore material. The resin is preferably provided as a particulate suspension in water. The particle size of resin may be from 0.01 to 1.0 μm, preferable from 0.05 to 0.5 μm. DuPont T-30 60% PTFE suspended in water, particle size 0.05 to 0.5 μm, is preferred.

The membranes of this invention are preferably formed from a paste-like mixture of inorganic porous material, particulate synthetic resin and water. The mixture is then formed into a sheet, as by calendering, which is sintered. The amount of water required to produce a porous sheet of suitable rigidity that contains 50 to 80% porous material by weight appears to be a function of the pore volume of the inorganic porous material used. The following formula may be used to determine an appropriate quantity of water to provide one form of a PTFE-CPG membrane of the invention:

Water (ml)=weight of inorganic porous material (gm)×2.6 × pore volume (ml/gm).

One method for producing membranes of this invention includes the following steps:

1. Mix inorganic porous material, e.g., CPG, water and aqueous resin, preferably a dispersion of PTFE, with stirring to form a paste-like mass.
2. Gel the mass, with occasional stirring, between a temperature of 50–70° C. (preferably 65° C.) for a mixing time vary from 5 to 15 minutes (e.g., 8 minutes).

3. Calender the gelled mass through a gap of 1.5–2 mm (preferably 1.8 mm) into a sheet under a calender roll pressure of 80 to 500 PLI.
4. Fold the sheet, rotate 90°, and pass through the calender rolls again. Repeat this step as needed to provide generally uniform dispersion of the inorganic porous material in the resin. For example, six repetitions may produce a uniform CPG dispersion in PTFE.
5. Reduce the calender roll gap to produce a membrane of the desired thickness, e.g., 5 to 200 mils.
6. Sinter the sheet at 340–375° C. for 30 to 60 minutes.

Sintered sheets may then be subjected to surface modification, for example, by silanization to provide functional groups for the binding of biological moieties including cells and biomolecules. See, e.g., Grusha, supra and U.S. Pat. Nos. 3,383,299 and 4,554,088.

A general formula for the silicone compounds useful for silanization is: R—Si—X, where R represents an organic moiety with a terminal functional group such as an amino, hydroxyl, epoxy, aldehyde, sulfhydryl, phenyl, long chain alkyl or other group that will chemically react or physically absorb with the biological molecules and X may be a mono-, di- or trialkoxy or halide group which will react with the silanol groups on the surface of the inorganic material. The degree of silanization can be demonstrated through quantitative analysis of the respective functional groups.

The following examples are intended to be illustrative of the invention and not in limitation. All parts and percentages are by weight, unless otherwise directed.

EXAMPLE 1

A mixture of 6 gm CPG (200/400 mesh, pore volume 0.87 cc/gm mean pore size 489 Å), 3.4 gm aqueous PTFE (~60% solid, DuPont T-30), and 13.5 ml water was stirred to provide a homogenous paste. The paste was heated in a beaker to form a dough at a temperature of ~60° C. for a mixing time of approximately 8 minutes. The dough was then passed through steel calendering rolls with a gap approximately 1.8 mm at a pressure of approximately 120 PLI to form a sheet. The calendered sheet was folded, rotated 90°, and repassed through the 1.8 mm gap. This step was repeated for at least six times to produce uniform particle distribution. The sheet was then sintered at 340° C. for 30 minutes to provide a rigid, porous sheet.

The 60 mils thick CPG-PTFE sheet has a flow rate at 10 psi of 66 ml/min/cm$^2$ using a 13 mm disc in a plastic Swinney housing. Sheets of different thickness are produced by changing the calender roll gap.

EXAMPLE 2

Example 2 illustrates that the amount of water needed in the formulation of the membrane is a function of pore volume. CPG of the same pore diameter particle size (200/400 mesh as shown in Example 1) but having different pore volumes is utilized to compensate for the water which fills the pores. The higher the pore volume of CPG particle, the more water is needed to produce the same flow characteristic of the membrane.

| SAMPLE # | 2 | 3 | 4 | 5 | 6 | 7 | 8 |
|---|---|---|---|---|---|---|---|
| Pore Volume (cc/gm) | 1.32 | 1.29 | 1.19 | 1.15 | 0.94 | 0.85 | 0.72 |
| Water Needed (ml) | 21 | 20 | 18 | 18 | 15 | 13 | 11 |
| Flow Rate (ml/min) | 68 | 66 | 68 | 66 | 66 | 66 | 66 |

EXAMPLE 3

Example 3 illustrates the relationship between flow rate and CPG pore diameter. 200/400 mesh CPG was used in all experiments. Pore size below 120 Å had a much slower flow rate than the pore size above 350 Å. No significant difference in flow rate was observed between 500 to 2000 Å.

| Flow Rate Table at 10 Psi | |
|---|---|
| CPG Pore Diameter(Å) | Acetonitrile flow rate (ml/min at 10 psi) |
| 75 | 28 |
| 120 | 28 |
| 350 | 66 |
| 500 | 70 |
| 700 | 72 |
| 1000 | 74 |
| 2000 | 72 |

EXAMPLE 4

Example 4 shows large particle size CPG of the same pore size improves membrane flow rate.

| CPG Lot # | Pore Diameter | Particle Size, μm | Flow rate (ml/min at 10 psi) |
|---|---|---|---|
| 06F16001 | 565Å | 30 | 20.5 |
| 06F16004 | 565Å | 15 | 16.5 |
| 06F16008 | 565Å | 10 | 16.0 |
| 06F16015 | 565Å | 7 | 9.0 |

EXAMPLE 5

Affinity Chromatography

1. Preparation of functionalized Protein A Disc:

A 47 mm×60 mils thick membrane of the invention is prepared as described herein from 200/400 mesh CPG having a pore diameter of about 500 Å. A disc from that membrane was assembled in a Millipore Swinnex holder and connected to a peristaltic pump for recirculation. To provide a NH$_2$ group on the disc surface, 50 ml of 5% aminopropyl-triethoxysilane (OSI A-1100) in methanol was pumped through the disc and recycled for three hours with a flow rate of 30 ml/min. The disc was then flushed sequentially with 100 ml methanol, and with 200 ml water. 50 ml of 5% glutaraldehyde aqueous solution (pH 7.2) was then recycled through the disc for one hour. Following flushing with 200 ml of 10 mM phosphate buffer (pH 7.2), the disc is ready for protein A attachment to (CHO) the aldehyde groups provided on the surface thereof. 14.6 mg of protein A was dissolved in 15 ml of 10 nM phosphate buffer and recycled through the disc for one hour. 10.7 mg of protein A was found covalently bond to the disc by measuring both feed and effluent at 280 nm.

2. Affinity chromatographic use of the Protein A disc:

10 mg of rabbit IgG (technical grade, Sigma I 8140) was dissolved in a 10 ml phosphate buffer and recycled through the Protein A disc in a 47 mm Millipore Swinnex folder for 30 minutes. The bound IgG was eluted with 2% acetic acid. The amount of IgG in both effluent and eluant were measured at 280 nm on the Bausch & Lomb spectronic 1001.

Results:

IgG challenged—10 mg bound—7.30 mg eluted—5.91 mg

% recovery—81%

EXAMPLE 6

Ion Exchange Chromatography

A 47 mm×60 mils thick membrane disc as described in Example 5 was assembled in a Millipore Swinnex holder and connected to a peristaltic pump for recirculation. 50 ml of 5% polyethylenimine (PEI, Virginia Chem. P-600) aqueous solution was pumped through a 47 mm×60 mils disc and recycled for two hours. This "PEI" disc was flushed with 500 ml of water and dried at 40° C. The PEI disc was evaluated as a binder for bovine serum albumin (BSA, Sigma A-2153) binding.

20 mg of BSA was dissolved in a 20 ml of 10 mM phosphate (pH 7.2) buffer and recycled through the PEI disc for one hour. The bound BSA was eluted with 1.0 M NaCl.

Results

BSA challenged—20 mg

BSA bound—19 mg 16.55 mg was eluted form the 19 mg bound BSA to give a 87.1% recovery using a high ion strength 1.0 M NaCl eluting solution.

EXAMPLE 7

DNA Syntheses Application

1. Preparation of the dA nucleotide coated disc:

150 pieces of 7 mm×60 mils thick membrane disc as described in Example 5 and 150 ml of 10% γ-glycidoxypropyltrimethoxysilane (OSI Silquest A-187) in toluene solution were placed in a flask with slowly stirring and heated to reflux for 48 hours to provide epoxide groups on the disc surface. The epoxide groups on the disc surface were hydrolyzed to provide diols which were then oxidized with sodium periodate (150 ml, 11.8 gm NaIO4 in water, at 40° C. for six hours). The discs were then treated with 1,6-hexanediamine in sodium bicarbonate solution to provide amino groups on the disc surfaces (150 ml total, 5 ml hexanediamine and 11.2 gm NaHCO3 in water, pH 10.5, for three hours). Twenty-five pieces of the resultant amino discs and the following chemicals were placed in a test tube and tumbled for twenty hours to provide the dA coated discs:

| | |
|---|---|
| 5'-0-DMT-3'-0-succinic acid-2'-deoxy adenosine(N$^6$ benzoyl) | 139.9 mg (dA) |

-continued

| | |
|---|---|
| Ethyl-3(3-Dimethlyamino) propyl carbodiimide | 70.62 mg |
| Dimethylaminopyridine | 11.26 mg |
| Triethylamine | 6.24 μl |
| Dimethylformamide | 4.0 ml |
| Pyridine | 1.0 ml |

2. DNA synthesis evaluation.

Oligonucleotides of 19 bases sequence were synthesized on the dA discs by using an ABI Snapped column with one frit on the upper side and ABI Synthesizer model 381 A according to the manufacturing protocol.

Results

Disc 1 DMTr Capacity=49.1 μmole/g

Synthesis Efficiency=97.7%

Disc 2 DMTr Capacity=47.7 μmole/g

Synthesis Efficiency=98.4%

EXAMPLE 8

Preparation of Amino Controlled Pore Glass PTFE Membrane 7 mm discs are punched out from the membrane prepared as described in Example 5 and dried under vacuum at room temperature for two hours. 100 pieces of the dried membrane discs are placed in a three neck round bottom flask. 150 ml of 10% gamma-aminopropyltriethoxysilane in dry toluene is added to the flask. The disc is gently stirred under refluxing condition for 24 hours. The discs are then washed with methanol for five times to remove excessive silane and baked in the oven at 90° C. for eight hours.

EXAMPLE 9

Preparation of Controlled Pore Glass—PTFE Epoxide Membrane 100 pieces of the 7 mm membrane disc prepared as described in Example 5 are placed in a three neck round bottom flask. 150 ml of 10% 3-glycidoxypropyltrimethoxysilane in dry toluene is added to the flask. The disc is gently stirred under refluxing condition for 24 hours. The membrane discs are then washed with methanol and acetone to remove excessive silane and baked in the oven at 100° C. for 16 hours.

EXAMPLE 10

Coupling of Anti-HBsAg to Amino-CPG/PTFE Membrane 25 pieces of amino CPG/PTFE membrane, prepared as described in Example 8, is added to a bottle containing 30 ml of 10% aqueous glutaraldehyde at pH-7.0. The disc is shaken gently for one half hour at room temperature. 30 mg of sodium borohydride is then added and the disc is then shaken in an ice-water bath for three hours. At the end of the reaction, the membrane discs are washed with phosphate buffer thoroughly. The amino groups on the surface of the discs are thus converted to aldehyde moieties.

9.9 ml (1 mg/ml protein conc.) of crude goat anti-human hepatitis B surface antigen (anti-HBsAg) antibody solution (Electro-Nucleonics Laboratory, Inc.) is added to 25 pieces of the aldehyde bearing discs and 12 mg of sodium borohydride. 0.1 M sodium carbonate of pH=9.5 is used to adjust the pH of the mixture to 8.5. The disc is shaken in the refrigerator for 24 hours. The antibody coupled discs are then washed three times with 0.1 M sodium phosphate buffer, pH=7.5 (five times). To block any active sites from residue silanol, amino or aldehyde groups, 5 ml (2 mg/ml) human serum albumin solution is treated with the antibody coated discs for three more hours. The antibody coated disc is washed with phosphate buffered saline (PBS) three times, 1M NaCl once, and again with PBS three more times. The discs are then stored in the refrigerator for use in immunoassay procedures.

EXAMPLE 11

Preparation of Nucleoside CPG/PTFE Membrane dT-CPG/PTFE membrane is prepared to demonstrate the production of nucleoside CPG/PTFE membranes. Deoxythymidine (dT) is used in this example. dA, dC and dG CPG products are produced in like manner.

50 pieces of dried epoxide CPG/PTFE membrane prepared in Example 9 is placed in a 100 ml round bottom flask. 5 gram of 1,6-hexanediamine in 50 ml of dried methanol is added. The disc is stirred gently at room temperature for three hours. At the end of the reaction, the disc is washed with methanol, 0.05 m sodium acetate buffer of pH 5.5, then deionized water, then final methanol wash before it is dried. The long chain amino disc is found to have 35 micromole of primary amine per gram of solid. 50 pieces of this long chain amino disc, 160 mg of DMTr-deoxythymidine succinic acid, 0.160 ml 1,3-diisopropylcarbodiimide, 2.2 mg 4-dimethylaminopyridine, 1 ml pyridine and 4 ml N,N-dimethylformamide are mixed together in a 8 ml amber vial. The vial is placed on an orbitory shaker for shaking 24 hours at room temperature. At the end of the reaction, the disc was capped with 0.1 ml acetic anhydride for three hours followed by quenching the excessive anhydride with 0.2 ml dried methanol in ice-bath for another three hours. The DMTr-thymidine disc (DMTr-dT-CPG) is then washed with N,N-dimethylformamide, methanol and dichloromethane before subjected to vacuum drying. The disc is quantified by cleaving the DMTr (dimethoxytrityl-) moiety from the dT disc with 3% p-toluenesulfonic acid in acetonitile and measure its absorbance at 504 nm.

EXAMPLE 12

Synthesis of 20-Mer Oligonucleotide with DMTr-deoxythymidine CPG/PTFE Membrane 10 mg of the dT-CPG from Example 11 is packed in a DNA reaction column. The column is placed in the DNA synthesizer of model 381A manufactured by Applied Biosystems, Inc. (ABI). β-cyanoethyl phosphoramidites and other synthetic reagents for synthesis are acquired from Applied Biosciences, Inc. A 20 mer oligonucleotide of the following sequence is synthesized, i.e., AGA/CAG/TCT/GAT/CTC/GAT/CT. The DMTr groups, which are removed in each synthesis cycle, are collected and measured at 504 nm to check for coupling efficiency. The 20 mers are then cleaved off from the solid phase and subjected to HPLC analysis.

EXAMPLE 13

Synthesis of Non-Cleavable 25-Mer Oligonucleotide with Controlled Pore Glass/PTFE Membrane 50 pieces of epoxy CPG/PTFE membrane discs from Example 9 is hydrolized in 10 ml of acidic aqueous solution at pH=4.0 (adjusted with hydrochloric acid) and at 40° C. for two hours. At the end of reaction, the CPG/PTFE membrane discs were washed five time with 50 ml deionized water, because the epoxy group is converted into dihydroxyl group. This material is designed as glyceryl CPG/PTFE membranes. One disc of this material was then packed in a DNA synthesis column. The column was placed in the automatic DNA synthesizer of model 381A manufactured by Applied Biosystems Inc. Beta-cyanoethyl phosphoramidites and other reagents for synthesis are acquired from the same company. A 25-mer of deoxythymidine oligonucleotide of the following sequence is synthesized, i.e., TTT/TTT/TTT/TTT/TTT/TTT/TTT/TTT/T. The disc bearing the 25-mer was then subjected to the treatment of ammonium hydroxide to remove the phosphate protective groups. Due to the more stable phosphodiester linkage between the 25-mer oligonucleotide chain and the CPG in the membrane, a large fraction of the oligonucleotides remains covalently linked to the disc as confirmed by the DMTr groups and by the capability of the product to hybridize poly(dA)12 oligonucleotides. Products bearing the 25-mer are useful to purify mRNA and poly(da) immediately after synthesis. It is also useful in DNA assays. The CPG/PTFE membrane disc with non-cleavable synthetic oligonucleotides are also useful in DNA assays.

EXAMPLE 14

Preparation of Protein A Coated Magnetic Pore Glass/PTFE Membrane Useful as an Antibody Adsorbent One gram of the product of Example 9 (epoxy CPG/PTFE membrane) is placed in a vial containing 5 ml of 0.1 m sodium periodate aqueous solution. The vial is placed on a shaker and shook for 1 hour. At the end of reaction, the glass is washed with 5×5 ml deionized water. 15 mg of Protein A is dissolved in 5 ml of 0.01 M phosphate buffer of pH=7.2 and added to the glass. The vial is shaken gently in the refrigerator for 24 hours. At the end of coupling reaction, 0.02% (wt %) of sodium borohydride is added to the mixture, and the reaction is allowed to proceed for another two hours. pH is adjusted to around pH=8.5 to 9.0 with dilute hydrochloric acid or sodium hydroxide if necessary. At the end of the reaction, the glass is washed with 5×10 ml of phosphate buffer. The product is CPG/PTFE membrane particles coated with Protein A.

200 mg of the Protein A bearing particles were placed in a 8 ml vial which contains 5 ml of 10 mg goat anti-BSA (bovine serum albumin) antibody in 0.05 M phosphate buffer +0.15 M sodium chloride of pH=7.5. The vial is then shaken gently for one half hour at room temperature. The glass is then washed with 5×5 ml of the loading buffer to remove the excess or unbound proteins. To elute the absorbed-antibody from the Protein A magnetic glass, 3×1 ml of 0.1 M glycine/HCl buffer of pH=2.0 is used. The washing buffers are pooled together and the protein concentration measured by Lowry's method at 280 nm to determine the binding capacity in terms of the amount of goat anti-BSA (bovine serum albumin) antibody per gram of Protein A CPG/PTFE membrane.

The membranes of this invention are useful for all of the same purposes as both unmodified and functionalized CPG and similar porous materials.

What is claimed is:

1. A method of preparing a controlled pore glass—polytetrafluoroethylene ("PTFE") resin chromatography membrane, comprising:

(i) combining controlled pore glass and an aqueous dispersion of PTFE to form a glass—PTFE mixture, and stirring the mixture to form a paste-like mass, (ii) heating the paste-like mass at a temperature between about 50 to 70° C. to form a calenderable dough, (iii) calendering the dough to provide a foldable sheet of desired thickness, and (iv) sintering the calendered sheet at a temperature of between 340 to 375° C. for more than 30 minutes to form a rigid, porous chromatography membrane having a flow rate of 20 to 200 ml/min/cm2 at 10 psi of acetonitrile through a 13 mm diameter membrane disc in a plastic Swinney disc filter holder.

2. The method of claim 1 including the step of (v) silanizing said rigid, porous membrane.

3. The method of claim 1, including the step of adjusting the flow rate of the membrane by adding additional water when combining the inorganic porous material and synthetic resin when the pore volume of the porous material is higher.

4. The method of claim 1, including folding the calendered sheet and rotating the folded sheet and passing the folded and rotated sheet through the calender rollers at least one more time.

5. The method of claim 4, including repeating folding and rotating and passing through the calender rollers.

6. The method of claim 1, wherein said calendered sheet is sintered for more than 30 minutes, up to a time of 60 minutes.

* * * * *